United States Patent [19]
Collins

[11] Patent Number: 5,747,248
[45] Date of Patent: May 5, 1998

[54] DISCONTINUOUS PROBE DESIGN USING HYBRITOPE MAPPING

[75] Inventor: Mark L. Collins, Walnut Creek, Calif.

[73] Assignee: Chiron Corporation, Emeryville, Calif.

[21] Appl. No.: 349,316

[22] Filed: Dec. 5, 1994

[51] Int. Cl.⁶ .............................. C12Q 1/68; C12Q 1/70
[52] U.S. Cl. ...................... 435/6; 435/5; 935/77; 935/78
[58] Field of Search ........................ 435/6, 5, 973; 536/23.2, 24.3, 23.1

[56] References Cited

FOREIGN PATENT DOCUMENTS

| WO 92/10588 | 6/1992 | WIPO . |
| WO 93/17126 | 9/1993 | WIPO . |
| WO 94/21825 | 9/1994 | WIPO . |

OTHER PUBLICATIONS

European Search Report for PCT Application No. US 95/15779.
Cload et al., *J. Am Chem Soc.* (1991) 116:6324–6326.
Cload et al., *J. Am Chem Soc.* (1994) 113:437–442.
Diekman et al, PNAS 84:8257–8261 (1987).
Chevrie et al, Nucleic Acid Res 18:6353–6359 (1990).
Cload et al, J. Am. Chem. Soc 116:437–442 (1994).
Dovdna et al, PNAS 86:7402–7406 (1989).
Cload et al, J. Am. Chem. Soc 115:5005–5014 (1993).

*Primary Examiner*—Eggerton A. Campbell
*Attorney, Agent, or Firm*—Kenneth M. Goldman; Robert P. Blackburn

[57] ABSTRACT

This invention provides a method of detecting or determining a binding oligonucleotide comprising a nucleotide sequence which binds within a known nucleotide sequence of a target nucleic acid using a technique called hybritope mapping. This invention also provides a method of using hybritope mapping to obtain discontinuous probes that bind to a target nucleic acid.

12 Claims, 9 Drawing Sheets

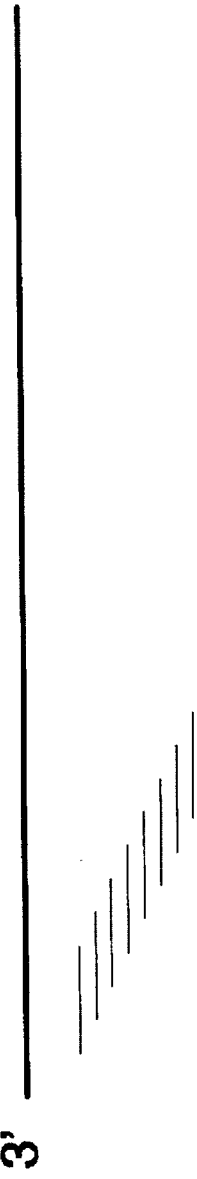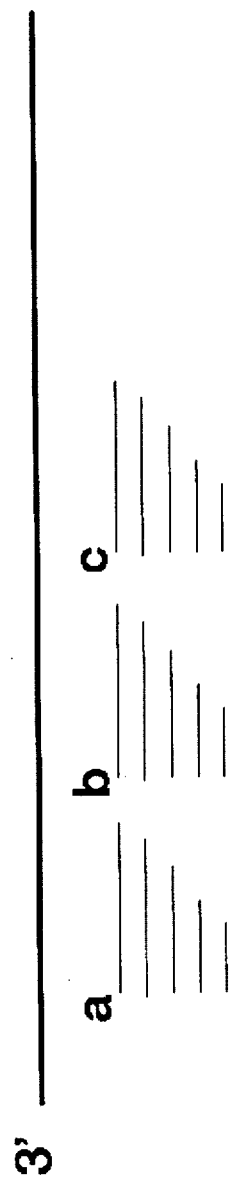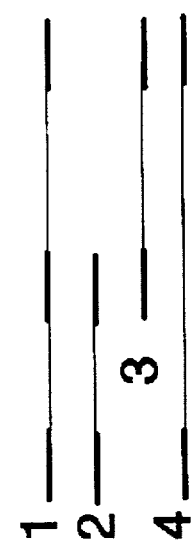
Figure 2A  Step 1: Find the optimal 5' end
Figure 2B  Step 2: Find the optimal 3' end (optimal length)
Figure 2C  Step 3: Make discontinuous probes

| Probe | Percent Cleavage | | |
|---|---|---|---|
| | 6mer | 8mer | 10mer |
| B6 | 53 | 75 | 80 |
| C6 | 7 | 21 | 68 |
| D7 | 12 | 54 | 74 |

FIGURE 5

| Probe Type/# | D7 targeted nts | D7 untarg. nts | C6 targeted nts | C6 untarg. nts | B6 targeted nts | RLU |
|---|---|---|---|---|---|---|
| Continuous | | | | | | |
| 1 | 13 | 0 | 12 | | 0 | 12 |
| 2 | 13 | 0 | 12 | | 12 | 20 |
| Two segments | | | | | | |
| 3 | 8 | 5 | 9 | | | 121 |
| 4 | 9 | 4 | 9 | | | 111 |
| 5 | 8 | 5 | 11 | | | 71 |
| 6 | 11 | 2 | 12 | | | 31 |
| 7 | 13 | 0 | 12 | | | 25 |
| Three segments | | | | | | |
| 8 | 7 | 6 | 10 | 2 | 9 | 164 |
| 9 | 8 | 5 | 8 | 4 | 8 | 129 |
| 10 | 7 | 6 | 7 | 5 | 7 | 88 |
| 11 | 10 | 3 | 10 | 2 | 9 | 40 |
| 12 | 10 | 3 | 11 | 1 | 10 | 30 |
| 13 | 10 | 3 | 11 | 1 | 12 | 11 |

FIGURE 7

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATAGTAGGAG    CTATGTTCCT    TGGGTTCTTG    GGAGCAGCAG    GAAGCACTAT    GGGCGCAGTG         6 0

TCATTGACGC    TGACGGTACA    GGCCAGACAA    TTATTGTCTG    GTATAGTGCA    ACA                1 1 3
```

( 2 ) INFORMATION FOR SEQ ID NO:2:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

GGTCCGTCGG NNNNNNNNNN NNNNNNNNNN NNNNNNNNNN NNNNNNNNNN NNNNNNNNNN    60

NNNNCTCTTG GAAAGAAAGT    80

( 2 ) INFORMATION FOR SEQ ID NO:3:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

CACTTCACTT TCTTTCCAAG AG    22

( 2 ) INFORMATION FOR SEQ ID NO:4:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

CCGACGGACC    10

DISCONTINUOUS PROBE DESIGN USING HYBRITOPE MAPPING

FIELD OF THE INVENTION

This invention is in the field of nucleotide probe and antisense probe chemistry. More specifically, this invention provides a method for determining a discontinuous probe that binds tightly to its nucleic acid target for use in diagnostics or as an antisense therapeutic. Discontinuous probes bind to two or more non-contiguous regions of a target nucleic acid and include antisense molecules, ribozymes, tethered probes and branched DNA molecules.

BACKGROUND OF THE INVENTION

Tools for sequence-specific recognition of DNA and RNA are increasingly important in the growing fields of nucleic acid probe technology, as well as antisense and ribozyme therapeutics. Sequence-specific recognition of RNA is especially challenging due to its complex conformational structure and intramolecular hybridization.

Cload and Schepartz, *J. Am. Chem. Soc.* (1991) 113: 6324–6326, disclose a family of synthetic molecules for the sequence- and structure-specific recognition of RNA called tethered oligonucleotide probes (TOPs). TOPs consist of two oligodeoxyribonucleotides separated by a flexible, synthetic tether. The two oligonucleotides bind to non-contiguous, single-stranded regions of the RNA molecule, and are tethered by a repeating abasic phosphodiester unit, or a repeating polyethylene glycol unit. The authors in this article do not suggest a method for selecting superior oligonucleotides to be tethered. Cload and Schepartz, *J. Am. Chem. Soc.* (1994) 116: 437–442, teach the use of a random oligonucleotide library to select superior oligonucleotides that bind to non-contiguous regions of a target RNA to be tethered together in a TOP. The authors, using a known Rev binding site in the human immunodeficiency virus (HIV) Rev response element (RRE), searched for a second oligonucleotide by tethering random heptanucleotides to an octanucleotide that bound to the Rev site, and screening with RNase H to determine the strongest site for secondary binding.

European Publication 0 138 855 describes a method of determining antigenically active amino acid sequences within a known protein by synthesizing a series of overlapping peptides corresponding to sequences in that protein, and then screening the peptides against antibody serum raised against the protein to determine which peptides react with the serum antibodies.

The inventors herein describe a method of determining superior sites for binding oligonucleotides to a target nucleic acid called "hybritope mapping." Hybritope mapping may be used to identify improved discontinuous probes with high binding constants.

SUMMARY OF THE INVENTION

In one aspect of this invention, a method of detecting or determining a binding oligonucleotide comprising a nucleotide sequence which binds within a known nucleotide sequence of a target nucleic acid is provided, the method comprising the steps of: (a) obtaining a plurality of oligonucleotides, each of the oligonucleotides comprising a first nucleotide sequence which is complementary to a sequence within the known nucleotide sequence, and the oligonucleotides having overlapping first nucleotide sequences wherein the first nucleotide sequence of each of the oligonucleotides in the plurality of oligonucleotides overlaps the first nucleotide sequence of another oligonucleotide in the plurality of oligonucleotides by from one to four nucleotides; (b) contacting each of the oligonucleotides with the target nucleic acid under conditions permitting specific hybridization of oligonucleotides to the target; and (c) detecting or determining the presence or absence of specific oligonucleotide-target binding between each of the oligonucleotides and the target nucleic acid to indicate whether each oligonucleotide binds within the known nucleotide sequence, thereby determining or detecting one or more binding oligonucleotides.

In another aspect of this invention, a method of detecting or determining a discontinuous probe that binds to a known nucleotide sequence in a target nucleic acid, the discontinuous probe comprising (i) at least two binding oligonucleotides that are each complementary to a distinct region of the target nucleic acid, covalently joined directly or by (ii) an organic linker molecule, the method comprising the steps of: (a) determining at least first and second binding oligonucleotides that are each complementary to first and second region of the target nucleic acid, the first and second binding oligonucleotides binding more strongly to the target nucleic acid than other oligonucleotides that are complementary to other regions of the target nucleic acid, and wherein the first and second regions are non-contiguous; (b) covalently linking two or more of the oligonucleotides determined in step (a) in at least two combinations, directly or through organic linker molecules to obtain a set of candidate discontinuous probes; (c) contacting each candidate discontinuous probe with the target nucleic acid under conditions permitting specific hybridization of oligonucleotides to the target; and (d) detecting or determining the presence or absence of specific discontinuous probe-target binding between each of the discontinuous probes and the target nucleic acid to indicate whether each discontinuous probe binds the target nucleic acid, thereby determining or detecting one or more discontinuous probes.

In a preferred aspect of the above method for detecting a discontinuous probe, step (a) comprises the steps of: obtaining a plurality of oligonucleotides, each of the oligonucleotides comprising a first nucleotide sequence which is complementary to a sequence within the known nucleotide sequence, and the oligonucleotides having overlapping first nucleotide sequences wherein the first nucleotide sequence of each of the oligonucleotides in the plurality of oligonucleotides overlaps the first nucleotide sequence of another oligonucleotide in the plurality of oligonucleotides by from one to four nucleotides; contacting each of the oligonucleotides with the target nucleic acid under conditions permitting specific hybridization of oligonucleotides to the target; detecting or determining the presence or absence of specific oligonucleotide-target binding between each of the oligonucleotides and the target nucleic acid to indicate whether each oligonucleotide binds within the known nucleotide sequence, thereby determining or detecting one or more binding oligonucleotides; and selecting at least two binding oligonucleotides that bind most strongly to the target nucleic acid.

BRIEF DESCRIPTION OF THE DRAWINGS

FIG. 2 depicts a method of optimizing discontinuous probes of the current invention.

FIG. 5 shows the results of an experiment to confirm the binding of candidate binding oligonucleotides to the HIV RRE region by RNAse H cleavage.

FIGS. 7 and 8 show the results of the experiment shown in FIG. 6.

DETAILED DESCRIPTION OF THE INVENTION

Figure 1:
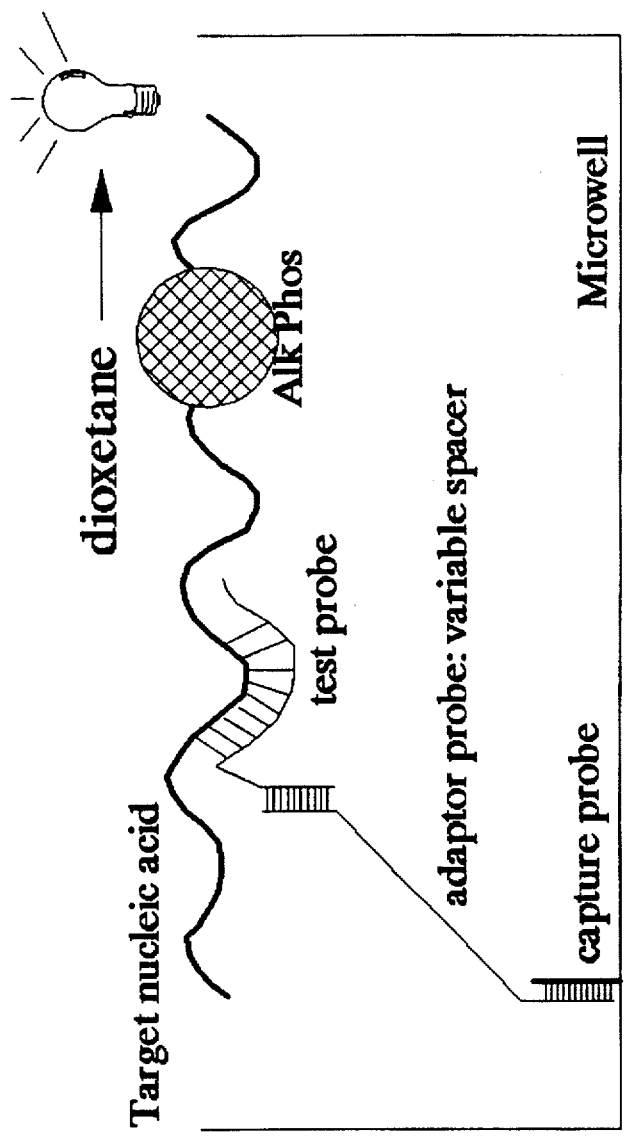
FIG. 1 depicts a hybritope mapping assay of the current invention.

The invention described herein draws on previously published work and pending patent applications. By way of example, such work consists of scientific papers, patents or pending patent applications. All of these publications and applications, cited previously or below are hereby incorporated by reference. Standard abbreviations for nucleotides and amino acids are used in this specification.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed. 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Definitions:

The term "antisense" refers to a nucleic acid molecule, preferably DNA, which is complementary to and capable of forming double stranded complexes with a "sense" strand of an RNA or DNA molecule. Hybridization of an antisense nucleic acid to mRNA, for example, inhibits its translation into proteins. Antisense nucleic acids may be protective (if they complement a viral protein mRNA or mRNA transcribed from an active oncogene, for example), or destructive (if they complement an essential host cell enzyme, such as a housekeeping enzyme with no effective alternate pathway). See also G. Zon et al. EP 288,163, which discloses the use of oligodeoxynucleotides for inhibition of retroviral replication and oncogenic proliferation.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, X-ray diffraction or absorption, magnetism, enzymatic activity, and the like. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase (HRP) is usually detected by its ability to convert 3,3',5,5'-tetramethylbenzidine (TMB) to a blue pigment, quantifiable with a spectrophotometer. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a monoclonal antibody (MAb). Further, one may combine various labels for desired effect. For example, MAbs and avidin also require labels in the practice of this invention: thus, one might label a probe with biotin, and detect its presence with avidin labeled with $^{125}I$, or with an anti-biotin MAb labeled with HRP, or with an HRP molecule conjugated to avidin or streptavidin. Other permutations and possibilities will be readily apparent to those of ordinary skill in the art, and are considered as equivalents The term "oligonucleotide" or "polynucleotide" as used herein refers to diagnostic probes, antisense probes, oligomer fragments to be detected, oligomer controls or ribozymes, and is defined as a molecule comprised of two or more deoxyribonucleotides or ribonucleotides, preferably more than three. Its exact size will depend on many factors, which in turn depend on the ultimate function or use of the oligonlcleotide. As used herein, the terms "polynucleotide", "oligonucleotide" and "nucleic acid" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing non-nucleotidic backbones (e.g., protein nucleic acids and synthetic sequence-specific nucleic acid polymers commercially available from the Anti-Gene Development Group, Corvallis, Oregon, as Neugene™ polymers) or nonstandard linkages, providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside", "nucleotide" and "nucleic acid" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

As used herein, a polynucleotide "derived from" a designated sequence refers to a polynucleotide sequence which is comprised of a sequence of approximately at least about 6 nucleotides, preferably at least about 8 nucleotides, more preferably at least about 10–12 nucleotides, and even more preferably at least about 15–20 nucleotides corresponding to a region of the designated nucleotide sequence. "Corresponding" means homologous, complementary, or substantially complementary to the designated sequence. The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends exact complementarity wherein each base within the binding region corresponds exactly, and "substantially complementary" intends 90% or greater homology.

As used herein, the term "oligomer" refers to both primers and probes and is used interchangeably herein with the term "polynucleotide." The term oligomer does not connote the size of the molecule. However, typically oligomers are no greater than 1000 nucleotides, more typically are no greater than 500 nucleotides, even more typically are no greater than 250 nucleotides; they may be no greater than 100 nucleotides, and may be no greater than 75 nucleotides, and also may be no greater than 50 nucleotides in length.

As used herein, the term "probe" refers to a structure comprised of a polynucleotide which forms a hybrid structure with a target sequence, due to complementarity of at least one sequence in the probe with a sequence in the target region. The polynucleotide regions of probes may be composed of DNA, and/or RNA, and/or synthetic nucleotide analogs. Included within probes are "capture probes" as will be defined below.

The term "capture probe" as used herein refers to a molecule comprising a single stranded polynucleotide coupled to a binding partner or solid support. The single-stranded polynucleotide region is complementary to a region of a second polynucleotide, and is sufficiently long and matched to afford sufficient affinity to immobilize the second polynucleotide to a solid support, directly or through a first binding partner specific for a second binding partner bound to the surface of a solid support.

The term "support" refers to any solid or semi-solid surface to which a specific binding partner may be anchored. Suitable supports include glass, plastic, metal, polymer gels, and the like, and may take the form of beads, wells, dipsticks, membranes, and the like. Presently preferred supports are provided as polystyrene beads or microtiter dish wells.

As used herein, the term "target region" or "target nucleotide sequence" refers to a probe binding region contained within the target molecule. The term "target sequence" refers to a sequence with which a probe will form a stable hybrid under desired conditions.

As used herein, the term "detecting or determining" an oligonucleotide probe or discontinuous probe refers to a method of selection wherein a pool of probes are assayed for a certain biological property, such as binding to a target. The object of determination is which probe or probes exhibits the best example of the desired property. For antisense probes, the desired property will preferably be strong binding. Probes useful for two-stage therapies (where a first drug is added, allowed to complex, and then a second effector molecule targeted at the complex is added) should exhibit persistent binding, which can be assayed by using low probe concentration for binding and applying increasingly stringent washes to elute the more weakly bound oligonucleotides. For ribozyme probes, the desired property will preferably be fast binding, which can be selected for by using low probe concentrations and short hybridization times.

As used herein, the term "ribozyme" refers to a polynucleotide that has the ability to catalyze the cleavage of a target nucleic acid substrate. In general, a ribozyme of the current invention will comprise a catalytic region, and at least one substrate binding region determined by the mapping technique described herein. Ribozymes are described generally in U.S. Pat. Nos. 5,144,019, 5,168,053, 5,180,818, 5,225,337 and 5,254,678. Catalytic regions of ribozymes are known in the art and include hammerhead, hairpin, hepatitis delta, and RNAse P type.

As used herein, the term "overlapping sequences" refers to two oligonucleotide sequences that share a partial common sequence. For example, the oligonucleotides GAATTC and AATTCC overlap in their common sequence AATTC. Because these two oligonucleotides both derive from the sequence GAATTCC, but have a starting point one nucleotide apart, the two nucleotides are said herein to overlap by one nucleotide.

As used herein, the term "discontinuous probe" refers to an oligonucleotide having two or more regions corresponding to two or more non-contiguous regions of a target nucleic acid. The two or more regions are covalently linked, either directly, through an intervening nucleotide sequence, or through an organic linker molecule. As used herein, the term "discontinuous probe" refers to two or more oligonucleotides covalently linked by an organic linker molecule. By "organic linker molecule" is meant an essentially linear spacer organic molecule capable of being attached at its two ends to two distinct oligonucleotides.

Hybritope Mapping

In one aspect of this invention, a method for detecting or determining the sequence or sequences of a target nucleic acid which constitute the best target region for an oligonucleotide probe is given. On the basis of this information, ideal probes for diagnostic detection of the target, or therapeutic molecules, such as an antisense probe or ribozyme, may be designed.

According to the present invention, the provided method comprises the steps of: (a) synthesizing or obtaining a plurality of oligonucleotides, each of the oligonucleotides comprising a first nucleotide sequence which is complementary to a sequence within the known nucleotide sequence, and the oligonucleotides having overlapping first nucleotide sequences wherein the first nucleotide sequence of each of the oligonucleotides in the plurality of oligonucleotides overlaps the first nucleotide sequence of another oligonucleotide in the plurality of oligonucleotides by from one to four nucleotides; (b) contacting each of the oligonucleotides with the target nucleic acid under conditions permitting specific hybridization of oligonucleotides to the target; and (c) detecting or determining the presence or absence of specific oligonucleotide-target binding between each of the oligonucleotides and the target nucleic acid to indicate whether each oligonucleotide binds within the known nucleotide sequence, thereby determining or detecting one or more binding oligonucleotides.

A. Test Probe Synthesis

The method of the present invention is based on the concept that a given target nucleic acid molecule, especially an RNA target, has certain regions containing nucleotide sequences that are more readily available for probe binding than other sequences located elsewhere on the target. By synthesizing a plurality, or pool of candidate oligonucleotide probes ("test probes") corresponding to overlapping segments of the target nucleic acid; incubating each member of the pool with the target; and determining the amount of probe-target binding, preferred probes are determined.

The test probe pool, or hybritope pool, consists of a set of oligonucleotide probes, each of which comprises a first target-binding sequence which is complementary to a nucleic acid sequence within the known target nucleic acid sequence. The set of oligonucleotide probes have overlapping nucleotide sequences wherein the first target-binding sequence of each of the oligonucleotides in the pool overlaps the first target-binding sequence of another oligonucleotide in the pool by from one to twenty nucleotides, preferably from one to four nucleotides, more preferably by one nucleotide. The region which is complementary to the known target nucleic acid sequence is generally from 6 to 30 nucleotides, more preferably from 8 to 24 nucleotides, still more preferably from 8 to 16 nucleotides. The test probes are preferably single stranded DNA molecules, optionally containing one or more phosphorothioate linkages or 2'-O-methyl groups.

Additionally, the test probes may contain other sequences that are useful in the assay for detecting target binding. For example, the oligonucleotide probes may optionally contain a second sequence which is an adapter probe recognition sequence having a nucleic acid sequence complementary to a test probe recognition sequence, which is used to capture the test probe directly or indirectly to a solid support. This region is generally from 6 to 30 nucleotides, more preferably from 8 to 24 nucleotides, still more preferably from 8 to 16 nucleotides. The test probes may also contain a third sequence which is a spacer sequence from I to 50 nucleotides, useful in spacing the first target-binding sequence from the second adapter probe recognition sequence.

The test probes are created by synthesis of individual oligonucleotides by known methods. Background references which relate generally to methods for synthesizing oligonucleotides include those related to 5'-to-3' syntheses based on the use of β-cyanoethyl phosphate protecting groups, e.g., de Napoli et al., *Gazz Chim Ital* (1984) 114: 65, Rosenthal et al., *Tetrahedron Lett* (1983) 24: 1691, Belagaje and Brush, *Nuc Acids Res* (1977) 10: 6295, in references which describe solution-phase 5'-to-3' syntheses include Hayatsu and Khorana, *J Am Chem Soc* (1957) 89: 3880, Gait and Sheppard, *Nuc Acids Res* (1977) 4: 1135, Cramer and Koster, *Angew Chem Int Ed Engl* (1968) 7: 473, and Blackburn et al., *J Chem Soc* (1967) Part C 2438.

Additionally, Matteucci and Caruthers, *J Am Chem Soc* (1981) 103: 3185–91 described the use of phosphochloridites in the preparation of oligonucleotides. Beaucage and Caruthers, *Tetrahedron Lett* (1981) 22: 1859–62, and U.S. Pat. No. 4,415,732 described the use of phosphoramidites for the preparation of oligonucleotides. Smith, *ABL* 15–24 (December 1983) describes automated solid-phase oligodeoxyribonucleotide synthesis. See also the references cited therein, and Warner et al., *DNA* (1984) 3: 401–11, the disclosures of which are incorporated herein by reference. T. Horn and M. S. Urdea, *DNA* (1986) 5: 421–25 described phosphorylation of solid-supported DNA fragments using bis(cyanoethoxy)-N,N-diisopropylaminophosphine. See also, T. Horn and M. S. Urdea, *Tetrahedron Lett* (1986) 27: 4705–08.

B. Test Probe Hybridization and Detection

Once the set of test probes pool has been synthesized, the individual test probes are brought in contact with the target nucleic acid under conditions permitting specific hybridization of test probe oligonucleotides to the target, and then determining the amount of binding for each probe-target pair. References which relate to hybridization techniques in general include the following: Meinkoth and Wahl, *Anal Biochem* (1984) 138: 267–84 (review of hybridization techniques); Leary et al., *Proc Natl Acad Sci USA* (1983) 80: 4045–49 (biotinylated DNA in conjunction with avidin-enzyme conjugates for detection of specific oligonucleotide sequences); Ranki et al., *Gene* 21: 77–85 (sandwich hybridization assay). Pfeuffer and Helmrich, *J Biol Chem* (1975) 250: 867–76 described the coupling of guanosine-5'-O-(3-thiotriphosphate) to Sepharose® 4B. Bauman et al., *J Histochem and Cytochem* 29: 227–37 described the 3'-labeling of RNA with fluorescers. PCT Application WO/8302277 described the addition to DNA fragments of modified ribonucleotides for labeling and methods for analyzing such DNA fragments. Renz and Kurz, *Nuc Acids Res* (19**) 12: 3435–44, described the covalent linking of enzymes to oligonucleotides. Wallace, *DNA Recombinant Technology* (Woo, S., ed.) CRC Press, Boca Raton, Fla., provided a general background of the use of probes in diagnosis. Chou and Merigan, *N Eng J of Med* 308: 921–25, described the use of a radioisotope-labeled probe for the detection of CMV. Inman, *Meth Enzymol* (1974) 34B, 24: 77–102, described procedures for linking to polyacrylamides, while Parikh et al., *Meth Enzymol* (1974) 34B, 24: 77–102, described coupling reactions with agarose. Alwine et al., *Proc Natl Acad Sci USA* (1977) 74: 5350–54 described a method of transferring oligonucleotides from gels to a solid support for hybridization. Chu et al., *Proc Natl Acad Sci USA* 11: 6513–29, described a technique for derivatizing terminal nucleotides. Ho et al., *Biochemistry* (1981) 20: 64–67 described derivatizing terminal nucleotides through phosphate to form esters. Ashley and MacDonald, *Anal Biochem* (1984) 140: 95–103 reported a method for preparing probes from a surface-bound template. Hebert and Gravel, *Can J Chem* (1974) 52: 187–89 and Rubinstein et al., *Tetrahedron Lett*, (1975) 17: 1445–48 described the use of nitrophenyl-containing compounds as light-sensitive protecting groups. K. Groegke et al., *Helvetica Chimica Acta* (1990) 73: 608–617 disclosed the use of t-butyldimethylsilyl to protect a hydroxyl functionality.

In a preferred embodiment of this invention, test probe hybridization and detection is performed by modification of methods disclosed in U.S. Pat. Nos. 4,868,105 and 5,124,246 to Urdea et al. Such solution phase sandwich hybridization assays are performed generally as follows and as shown in FIG. 1. In each assay, single-stranded target nucleic acid is incubated under hybridization conditions with an excess of two single-stranded nucleic acid probes: (1) a test probe as described above, having a first binding nucleotide sequence complementary to the target and a second binding sequence that is an adapter probe recognition sequence; and (2) an adapter probe having a first binding sequence that is a test probe recognition sequence complementary to the adapter probe recognition sequence on the test probe, a second binding sequence that is capable of specific hybridization to an oligonucleotide bound to a solid phase, and optionally containing a spacer sequence of 1 to 50 nucleotides. The resulting product is a three component nucleic acid complex of the test probe sandwiched between the target and the adapter probe. The second binding sequence and the optional spacer sequence of the adapter probe remains as a single-stranded tail.

Under hybridizing conditions, this complex is then added to (or incubated simultaneously with) a solid phase having a capture probe bound to it. The capture probe is a single-stranded oligonucleotide that is substantially complementary to the second binding sequence of the adapter probe. The resulting product comprises the complex bound to the solid phase via the duplex formed by the capture probe bound to the solid phase and the second binding sequence of the adapter probe. The solid phase with bound complex is then separated from unbound materials by washing.

The binding sequence of the adapter probe that is a test probe recognition sequence substantially complementary to the adapter probe recognition sequence on the test probe will be of at least 5 nucleotides, usually at least 10 nucleotides, and not more than about 20 nucleotides. It will typically be approximately 10 nucleotides.

The second binding sequence of the adapter probe is selected to be substantially complementary to the oligonucleotide attached to the solid phase and so as to not be encountered by endogenous sequences in the target. The second binding sequence may be contiguous to the first binding sequence or be spaced therefrom by an intermediate noncomplementary spacer sequence of between 0 to 50 nucleotides. The use of a short spacer region (or none at all) of 1 to 10 nucleotides, hinders extension of the test probe into the interior of target nucleic acid molecules when bound to the solid support through the adapter probe, and is thus preferable when determining test probes that bind only to external surfaces of target molecules. The probe may include other noncomplementary sequences if desired. These noncomplementary sequences must not hinder the binding of the binding sequence or cause nonspecific binding to occur. The adapter probe may be prepared by oligonucleotide synthesis procedures or by cloning, preferably the former.

The solid phase that is used in the assay may be particulate or be the solid wall surface of any of a variety of containers, e.g., centrifugal tubes, columns, microtiter plate wells, filters, tubing, etc. When particles are used, they will preferably be of a size in the range of about 0.4 to 200 microns, more usually from about 0.8 to 4.0 microns. The particles may be any convenient material, such as latex, or glass. Microtiter plates are a preferred solid surface. The oligonucleotide that is substantially complementary to the second binding sequence of the adapter probe may be stably attached to the solid surface through functional groups by known procedures.

It will be appreciated that one can replace the second binding sequence of the adapter probe and the oligonucleotide attached to the solid phase with an appropriate ligand-receptor pair that will form a stable bond joining the solid phase to the first binding sequence of the capture probe. Examples of such pairs are biotin/avidin, thyroxine/thyroxine-binding globulin, antigen/antibody, carbohydrate/lectin, and the like.

The ratio of adapter probe and test probe to anticipated moles of target will each be at least stoichiometric and preferably in excess. This ratio is preferably at least about 1.5:1, and more preferably at least 2:1. It will normally be in the range of 2:1 to $10^6$:1. Concentrations of each of the probes will generally range from about $10^{-9}$ to $10^{-2}$M, with sample nucleic acid concentrations varying from $10^{-10}$ to $10^{-8}$M. The hybridization steps of the assay will generally take from about 10 minutes to 20 hours, frequently being completed in about 1 hour. Hybridization can be carried out at a mildly elevated temperature, generally in the range from about 20° C. to 80° C., more usually from about 35° C. to 70° C., particularly 65° C.

The hybridization reaction is usually done in an aqueous medium, particularly a buffered aqueous medium, which may include various additives. Additives which may be employed include low concentrations of detergent (0.1 to 1%), salts, e.g., sodium citrate (0.017 to 0.17M), Ficoll, polyvinylpyrrolidone, carrier nucleic acids, carrier proteins, etc. Nonaqueous solvents may be added to the aqueous medium, such as dimethylformamide, dimethylsulfoxide, alcohols, and formamide. These other solvents are generally present in amounts ranging from 2 to 50%.

The stringency of the hybridization medium may be controlled by temperature, salt concentration, solvent system, and the like. Thus, depending upon the length and nature of the sequence of interest, the stringency will be varied. Preferred hybridization conditions, approximating physiological conditions, are 37° C., 0.15M monovalent cation, 16 mM $Mg^{++}$, and 1 mM spermidine.

The procedure used in the separation steps of the assay will vary depending upon the nature of the solid phase. For particles, centrifugation or filtration will provide for separation of the particles, discarding the supernatant or isolating the supernatant. Where the particles are assayed, the particles will be washed thoroughly, usually from one to five times, with an appropriate buffered medium, e.g., phosphate buffered saline (PBS) containing a detergent such as SDS. When the separation means is a wall or support, the supernatant may be isolated or discarded and the wall washed in the same manner as indicated for the particles.

The complex is then detected by labeling of the target in the bound complex. The target may be labeled before or after complex formation. The labeled target will include one or more molecules ("labels"), which directly or indirectly provide for a detectable signal. The labels may be bound to individual members of the target sequence or may be present as a terminal member or terminal tail having a plurality of labels. Various means for providing labels bound to the sequence have been reported in the literature. See, for example, Leary et al., *Proc Natl Acad Sci USA* (1983) 80: 4045; Renz and Kurz, *Nucl Acids Res* (1984) 12: 3435; Richardson and Gumport, *Nucl Acids Res* (1983) 11: 6167; Smith et al., *Nucl Acids Res* (1985) 13: 2399; Meinkoth and Wahl, *Anal Biochem* (1984) 138: 267. The labels may be bound either covalently or non-covalently to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, $\alpha$-$\beta$- galactosidase, horseradish peroxidase, alkaline phosphatase, etc. In a preferred embodiment, the target sequence is labeled by incorporation of biotin-UTP for a fraction of the natural rUTP or dTTP nucleotides, and then incubated with streptavidin-conjugated alkaline phosphatase (AP).

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

After all hybridization assays have been performed with each member of the test probe pool, the members that indicate the highest degree of binding to the target are determined to be the best candidate probes. Alternatively, the method is used to identify the fastest hybridizers (by using short incubation periods and low concentration of probes) or most persistent hybridizers (by using low concentration of probes, and increasingly stringent wash conditions).

C. Test Probe Size Determination

Once a test probe has been identified by the above methods to be among the best candidates, further experiments may be performed to determine the ideal size for the first nucleotide sequence of the probe complementary to the target sequence. A pool of secondary test probes are synthesized by standard methods, having a sequence complementary to the same region of the target nucleic acid and an identical first end as the candidate test probe, but each member of the secondary test probe pool has a different second end, as shown in FIG. 2. Thus, a typical secondary test probe pool has a first nucleotide sequence that ranges in size from about 6 to 50, more preferably from about 6 to 18 nucleotides, spanning the region of the target nucleic acid identified by the best candidate test probe or probes. The secondary test probes are then screened for the highest degree of binding to the target as above.

Discontinuous Probes

The result of hybritope mapping as described above is the identification of two or more candidate probes of idealized sequence and length. In another aspect of this invention, two or more of the candidate probes are joined covalently together either directly or with organic linkers of varying length and composition, and then assayed as above to determine those that have the highest degree of binding to the target.

The discontinuous probes are constructed as the test probes hybritopes above, optionally containing a region having a nucleic acid sequence that is an adapter probe recognition sequence and/or a spacer region as defined above, and also containing two or more oligonucleotides covalently joined directly or by an organic spacer —Z—, wherein —Z— is attached to the oligonucleotide through a sugar, base or phosphate moiety, and is selected from the group consisting of arylene, $C_6$-$C_8$ aralkylene, $C_6$-$C_{18}$ aralkenylene, $C_6$-$C_{18}$ aralkynylene, $C_1$-$C_{30}$ alkylene, $C_1$-$C_{30}$ alkenylene, or $C_1$-$C_{30}$ alkynylene, containing 0 to 6 heteroatoms selected from the group consisting of O, S, N, Si and Se and 0 to 6 linkages selected from the group consisting of —CO—, —COO—, —CONH—, —NHCO—, —S—S—, —SO$_2$—, —CH(OH)—CH(OH)—, —CH(OR$^1$)—CH(OR$^1$)—, —O—PO(O$^-$)—O—, —O—PO(R$^1$)—, —O—PO(OR$^1$)—O—, —O—PO(OR$^1$)—R$^2$—, —PO(OR$^1$)—O—R$^2$ wherein R$^1$ is lower alkyl and R$^2$ is lower alkylene, —O—$((CH_2)_n$—A—$)_m$ and

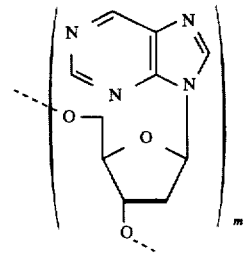

wherein —A— is —O— or —PO$_4$—, n is an integer from 2 to 4 and m is an integer from 1 to 20.

Preferred embodiments of organic linkers are "rigid linkers" which are linkers that are limited in degree of flexibility. Rigid linkers are known in the art, and include linkers containing one or more double or triple bonds, or ring structures, including substituted or unsubstituted arylene, $C_6$-$C_{18}$ aralkylene, $C_6$-$C_{18}$ aralkenylene, $C_6$-$C_{18}$ aralkynylene, $C_1$-$C_{30}$ alkenylene, or $C_1$-$C_{30}$ alkynylene.

A pool of discontinuous probes is then constructed selecting different combinations of the best candidate test probes and varying lengths and types of linker. For example, if hybritope mapping identifies four candidate test probe oligonucleotides A, B, C and D, then dual linked discontinuous test probes may be constructed as A-B, A-C, A-D, B-C, B-D and C-D. Tri-linked discontinuous test probes might also be constructed as A-B-C, A-C-B, B-A-C, A-B-D, A-D-B, etc., as shown in FIG. 2. The identity of the tethers might also be varied. Preferred tether variations are series of monomers joined together in various lengths. For example, one tether series is triethylene glycol, hexaethyleneglycol, nonaethylene glycol. Another series is

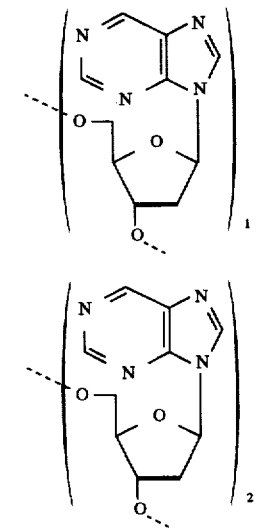

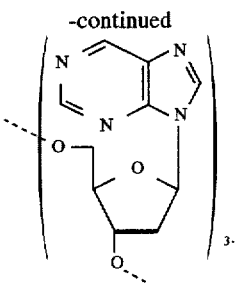

In another embodiment of this invention, discontinuous probes may be formed by attaching three or more candidate test probe sequences in a branched structure, using the branched DNA technology as set forth in U.S. Pat. No. 5,124,246 to Urdea et al. In the "branched discontinuous probes" formed by this technology, two candidate test probe sequences are joined by an organic linker molecule including a branching monomer as described in the '246 patent, which permits the joining of a third candidate test probe sequence. An example of a branched monomer having three attachment points is

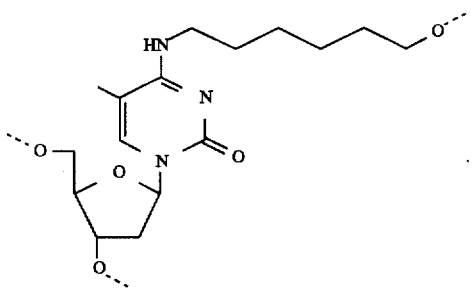

The constructed pool of discontinuous probes is then screened as above for those with highest binding to the target nucleic acid. The discontinuous probe with the highest degree of binding is then determined to be the best candidate probe. Alternatively, the method is used to identify the fastest hybridizers (by using short incubation periods and low concentration of probes) or most persistent hybridizers (by using low concentration of probes, and increasingly stringent wash conditions).

Use of Discontinuous Probes

Discontinuous probes may be used as diagnostic probes, as described for example in U.S. Pat. Nos. 4,868,105 and 5,124,246 to Urdea et al.

Discontinuous probes may also be formulated as antisense probes or ribozymes. As antisense probes, the discontinuous probes may be modified. Discontinuous antisense probes will not generally comprise a region having a nucleic acid sequence that is an adapter probe recognition sequence or a spacer region as described above. Additionally, the antisense nucleic acid of this invention is RNA, DNA or a modified nucleic acid. Examples, without limitation, of modified nucleic acids are degradation-resistant sulfurized and thiophosphate derivatives of nucleic acids, and polynucleoside amides (PCT Publication No. W091/16331 to Stec et al.; PCT Publication No. WO88/07544 to Zon et al.; P. E. Nelsen, et al., *Science* (1991) 254: 1497–1500; M. Egholm, *JACS*, (1992) 114: 1895–1897). Particularly preferred design modifications of the antisense nucleic acids of this invention are modifications that are designed to: (1) increase the intracellular stability of the nucleic acid; (2) increase the cellular permeability of the nucleic acid; (3) increase the affinity of the nucleic acid for the sense strand, or (4) decrease the toxicity (if any) of the nucleic acid. Many such modifications are known in the art, as described in ANTISENSE RESEARCH AND APPLICATIONS (S. T. Crooke and B. Lebleu, eds., CRC Press, 1993). Thus, the nucleic acids may contain altered or modified bases, sugars or linkages, be delivered in specialized systems such as liposomes, or may have attached moieties. Such attached moieties include hydrophobic moieties such as lipids that enhance interaction with cell membranes, or polycationic moieties such as polylysine that act as charge neutralizers of the phosphate backbone. Particularly preferred lipids that may be attached are cholesterols. The moieties may be attached at the 3' or 5' ends of the nucleic acids, and also may be attached through a base, sugar, or internucleoside linkage.

Other moieties may be capping groups specifically placed at the 3' or 5' ends of the nucleic acids to prevent exonuclease degradation. Such capping groups include, but are not limited to, hydroxyl protecting groups known in the art, including glycols such as polyethylene glycols, tetraethylene glycol and the like.

Administration

The antisense or ribozyme compounds of the invention may be administered by a variety of methods, such as intravenously, orally, intramuscularly, intraperitoneally, bronchially, intranasally, and so forth. The preferred route of administration will depend upon the nature of the compound and the condition to be treated. Compounds may be administered orally if well absorbed and not substantially degraded upon ingestion. The compounds may be administered as pharmaceutical compositions in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, sustained-release patches, and the like. Alternatively, one may incorporate or encapsulate the compound in a suitable polymer matrix or membrane, thus providing a sustained-release delivery device suitable for implantation near the site to be treated locally. Other devices include indwelling catheters and devices such as the Alzet® mini-pump. Further, one may provide the compound in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The antisense compositions of the present invention may be prepared for pharmaceutical administration. Injection preparations and suppositories may usually contain 1–10 mg of the nucleic acid or nucleic acid analog per ampoule or capsule. For human patients, the daily dose is about 0.1–1, 000 mg, preferably 1–100 mg (from 10–20 mg/kg to 1000–2000 mg/kg body weight). However, the particular dose for each patient depends on a wide range of factors, for example, on the effectiveness of the particular nucleic acid or nucleic acid analog used, on the age, weight, general state of health, sex, on the diet, on the time and mode of administration, on the rate of elimination, combination with other medicaments jointly used and severity of the particular diseases to which the therapy is applied.

Pharmaceutical articles of manufacture, within the scope of the present invention, include articles wherein the active ingredients thereof are contained in an effective amount to achieve its intended purpose. A preferred range has been described above, and determination of the most effective amounts for treatment is within the skill of the art.

In addition to the nucleic acid and their sulfurized and phosphorothioated analogs of the present invention, pharmaceutical preparations may contain suitable excipients and auxiliaries which facilitate processing of the active compounds. The preparations, particularly those which can be administered orally and which can be used for the preferred type of administration, such as tablets, dragees, and capsules, and preparations which can be administered rectally, such as suppositories, as well as suitable solutions for administration parenterally or orally, and compositions which may be administered bucally or sublingually, may contain from 0.1 to 99% by weight of active ingredients, together with the excipient. A preferred method of administration is parenteral, especially intravenous administration.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyloleate or triglycerides. Aqueous injection suspensions may contain substances which increase the viscosity of the suspension, for example, sodium carboxymethyl cellulose, sorbitol, and/or dextran. Optionally, the suspension may also contain stabilizers.

Additionally, the compounds of the present invention may also be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as dicetylphosphate, stearylamine, or phosphatidic acid, and/or other materials of a hydrophobic nature. The diameters of the liposomes generally range from about 15 nm to 5 microns. Particularly preferred lipids for the preparation of liposomes and/or lipid suspensions are DOTMA and DOTAP.

DOTAP is commercially available from Boehringer Mannheim, or may be prepared following the methods described by L. Stamatatos et al., *Biochem* 27: 3917–25 (1988); H. Eibl et al., *Biophys Chem* 10: 261–71 (1979). DOTMA is commercially available under the name Lipofectin* (available from BRL, Gaithersburg, Md.), and is described by P. L. Feigner et al. *Proc Nat Acad Sci USA* 84: 7413–17 (1987).

The present invention will now be illustrated by reference to the following examples which set forth particularly advantageous embodiments. However, it should be noted that these embodiments are illustrative and are not to be construed as restricting the invention in any way.

EXAMPLES

Example 1

Hybritope Synthesis

A hybritope probe pool was generated corresponding to a 113-nucleotide region in the Rev response element (RRE) of the sf2 isolate of the human immunodeficiency virus (HIV) genome. This region includes nucleotides 7769–7881 in the HIV sf2 genome, and has the sequence (nt 7769) 5'-ATA GTA GGA GCT ATG TTC CTT GGG TTC TTG GGA GCA GCA GGA AGC ACT ATG GGC GCA GTG TCA TTG ACG CTG ACG GTA CAG GCC AGA CAA TTA TTG TCT GGT ATA GTG CAA CA-3' (SEQ ID NO:1) (nt 7881). The pool comprised 96 deoxyribonucleotide probes, each probe being a 28-mer. The 5' portion of each probe in the pool was identical and consisted of a 10-mer having the sequence 5'-CCG ACG GAC C-3'SEQ ID NO:4. This GC rich sequence hybridizes to an adapter probe which is used in binding to a solid support.. The 3' 18-mer portion of each probe hybridizes to a portion of the HIV RRE, each portion overlapping the sequence of another probe in the pool by one nucleotide. Probe 1, for example, has a 3' portion that hybridizes to nucleotides 7769–7786, probe 2 has a 3' portion that hybridizes to nucleotides 7770–7787, and so on, through probe 96, which has a 3' portion that hybridizes to nucleotides 7864–7881. The probe pool was synthesized by standard phosphoramidite chemistry by Genosys Biotechnologies, Inc. (The Woodlands, Tex.).

Example 2

Hybritope Mapping of the HIV RRE Region

A. Probe Synthesis

A hybritope probe pool corresponding to a 113 nucleotide region of the HIV RRE region was synthesized as described in Example 1. Adapter probes having the sequence 5'- G GTC CGT CGG -(N)$_{54}$-CT CTT GGA AAG AAA GT-3' (SEQ ID NO:2) were also synthesized using standard methods. The 5' end of the adapter probe hybridizes to the hybritope probes, the 3' end hybridizes to a capture probe bound to a solid support, and the middle is a 54 random base spacer region. The capture probe having the sequence 5'-CA CTT CAC TTT CTT TCC AAG AG-3' (SEQ ID NO:3) was synthesized and bound to microtiter plate wells at the 3' end.

B. Target Labeling

DNA plasmid pBKBH10S contains a 9.2 kb copy of the genome of the HXB2 strain of HIV lacking the LTR region. pBKBH10S was cut with Sac I, and full length RNA transcripts of the genome were made using T7 RNA polymerase and the 4 rNTPs, incorporating 1 biotinylated UTP for every 30 UTPs, yielding approximately 75 biotinylated UTPs per full length transcripts. The biotinylated nucleotides are capable of forming a conjugate with alkaline phosphatase linked to streptavidin.

C. Mapping Procedure

The 96 hybritope probe pool of Example 1 was used to map the HIV RRE region, using labeled target as prepared in Example 2-B, and 96-well microtiter plate coated with the capture probes as prepared in Example 2-A attached to each well. Target (10 femtomoles), 500 femtomoles of each of the test probes, and 1 picomole adapter probe were separately equilibrated in hybridization buffer (0.1M NaCl, 0.05M KOAc, 16 mM MgCl$_2$, 1 mM spermidine, 50 mM Tris-HCl pH 7.5, 0.2% acetylated BSA) at 37° C. for 1 hour. Target and probes were mixed and allowed to equilibrate for an additional hour. The wells were washed three times with wash P (0.5 x SSC, 0.1% SDS). Streptavidin-conjugated alkaline phosphatase (BMB, 1:10,000 dilution) was added and incubated for 5 minutes at 37° C. Three additional washes with wash P was followed with three washes of 0.5 x SSC.

Figure 3:
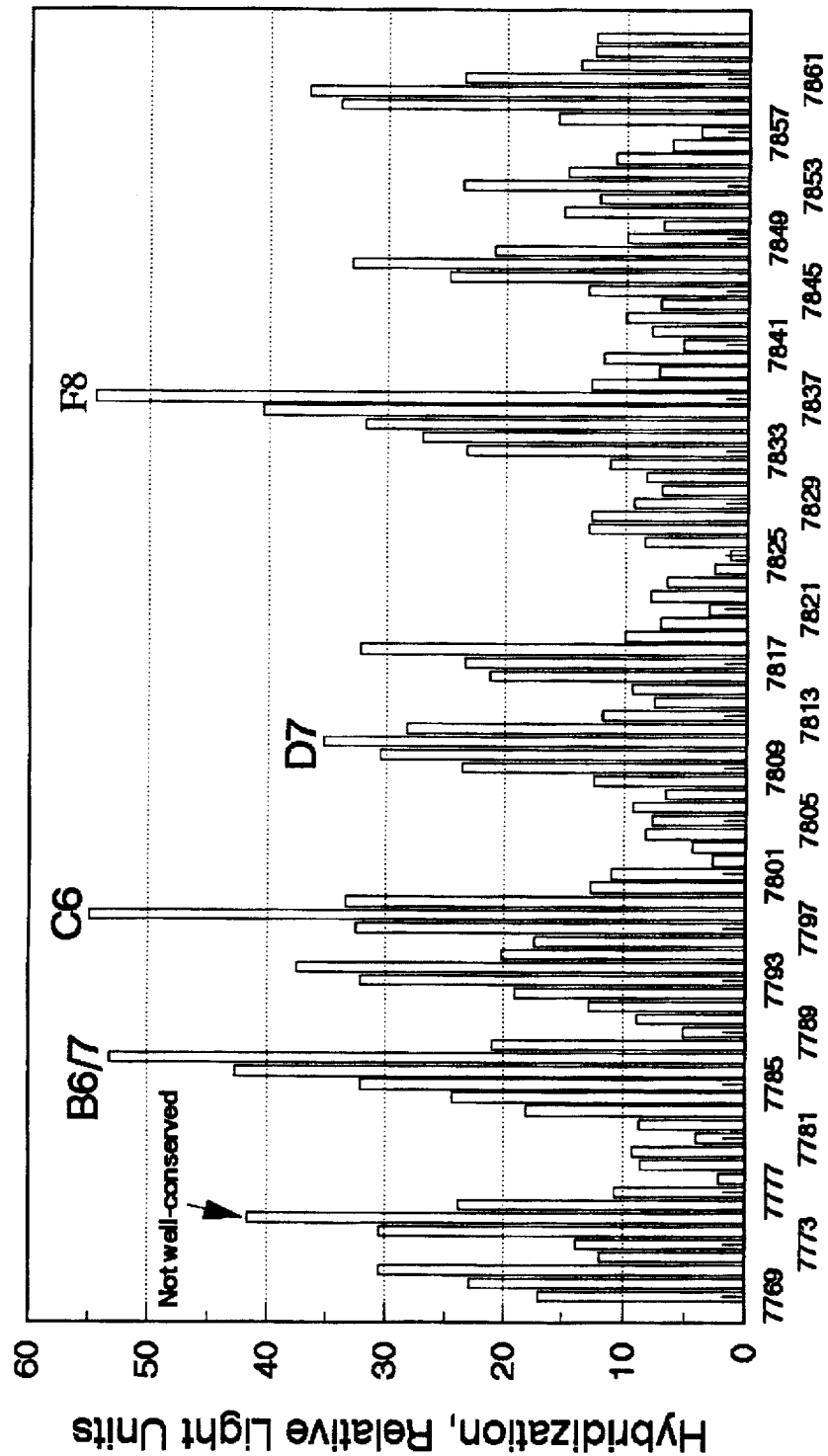
FIG. 3 shows the results of using the hybritope mapping method of the current invention to find the optimal oligonucleotides that bind to the HIV RRE region.

Lumiphos-plus™ (Lumigen, Southfield, Mich.) was then added to the dry wells at 50 µl/well, incubated at 37° C. for 30 minutes and luminescent light counts determined. The results of this assay on the 96 probe pool are shown in FIG. 3. Four hybritopes, labeled B6, C6, D7 and F8 were selected as the best binding 18mers. The HIV RRE regions complementary to these probes have the 5' end 7787, 7798, 7811 and 7837 respectively.

Example 3

Hybritope Size Optimization

A. Hybridization Analysis

Figure 4A:
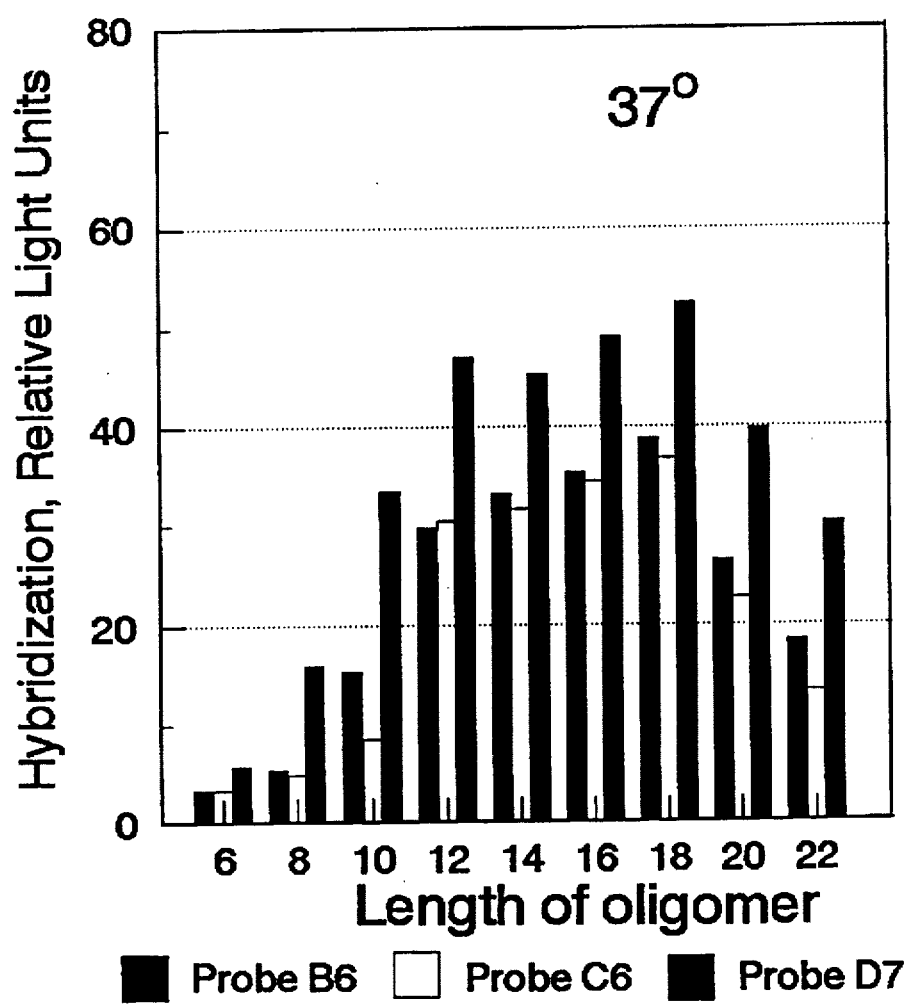
FIG. 4 shows the effect of oligonucleotide length on the ability of candidate binding oligonucleotides to bind the HIV RRE region.
Figure 4B:
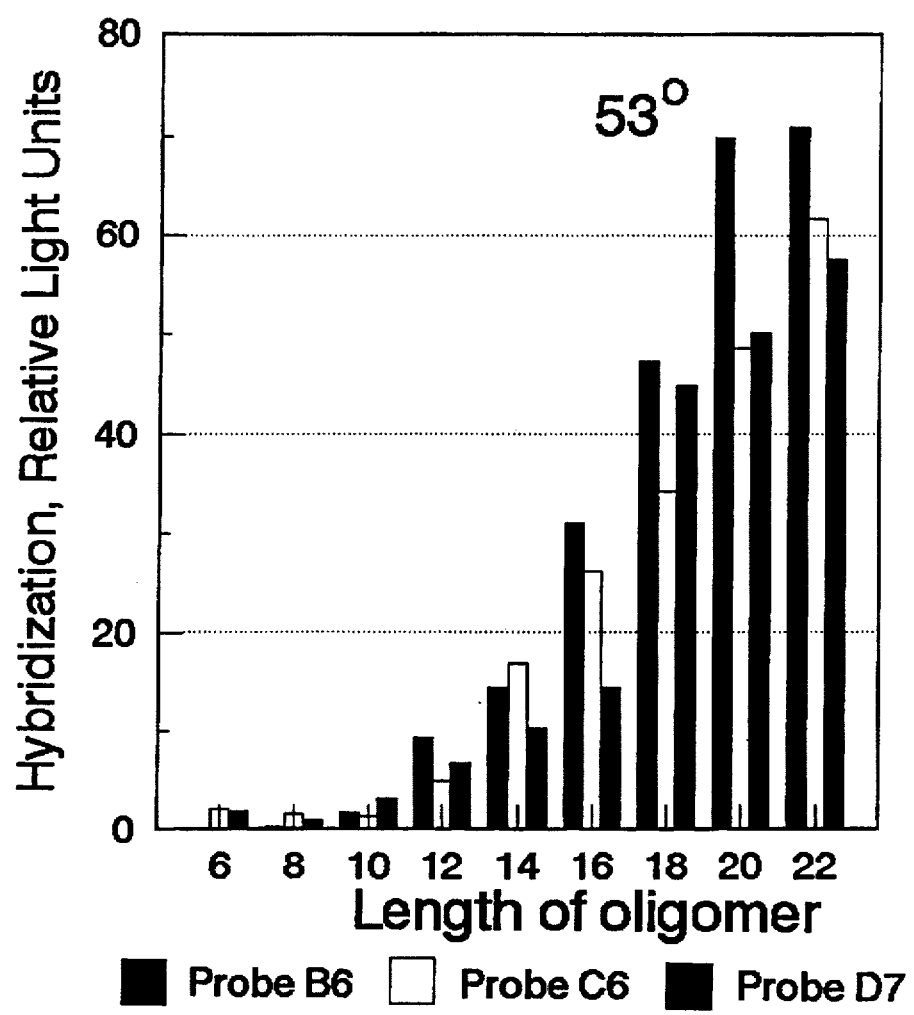

Three of the selected hybritopes in Example 2, B6 (7787), C6 (7798) and D7 (7811) were screened for size optimization. (numbers in parentheses indicate 5' end of complementary HIV RRE region) For each selected (primary) hybritope, a set of secondary hybritopes was synthesized. Each secondary hybritope contained the same 5' GC-rich region as the primary hybritope described in Example 1, and contained a 3' region hybridizing to the same region of the HIV RRE as the primary hybritope, beginning at the same 5' end, but varying in length from 6–23 nucleotides. These secondary hybritope pools were screened against HIV RRE target as described in Example 2, but parallel screenings were performed at 37° C. and at 53° C. The results are shown in FIG. 4. At physiological conditions, optimal hybritope lengths appear to be around 12 nucleotides, while the optimal length at 53° C. is around 20 nucleotides. Significant detectable binding of hybritopes of 10 nucleotides or less occurs at physiological temperatures, indicating a potentially significant source of non-specific hybridization if such lengths were used. Accordingly, RNAse H analysis was performed on the shorter secondary hybritopes.

B. RNAse H Analysis

A 205-mer HIV RRE RNA minitranscript was made from pBKBH10S using the Promega Riboprobe II Core System, incorporating $^{32}$P-GTP at a specific activity of $8\times10^6$ cpm/pmol. The minitranscript was run over a Nensorb column and eluted in 50% ethanol, precipitated, resuspended in water and stored frozen.

Each RNase H reaction contained $10^5$ cpm of minitranscript, preincubated at 37° C. for one hour in 20 μl buffer containing 50 mM Tris pH 7.5, 16 mM $MgCl_2$, 1 mM spermidine, 50 mM KOAc, 0.1M NaCl and 1 unit inhibitase (nuclease inhibitor). Individual secondary hybritopes were added at 0.5 μM and incubated at 37° C. for one hour. 10 units of RNase H was added to each reaction and incubated for 30 minutes. 5 μl of stop buffer (5% SDS, 250 ng/μl proteinase K, 75 mM EDTA) was added to each reaction and incubated at 65° C. for 15 minutes. Cleavage efficiency was calculated from the Ambis scan of the product run out on a 5% denaturing polyacrylamide gel. The results, shown in FIG. 5, demonstrate that significant hybridization of 6- and 8-mers occur at 37° C., but optimal probe selection will permit lower probe concentrations.

Example 4

Discontinuous Probes

Figure 6:
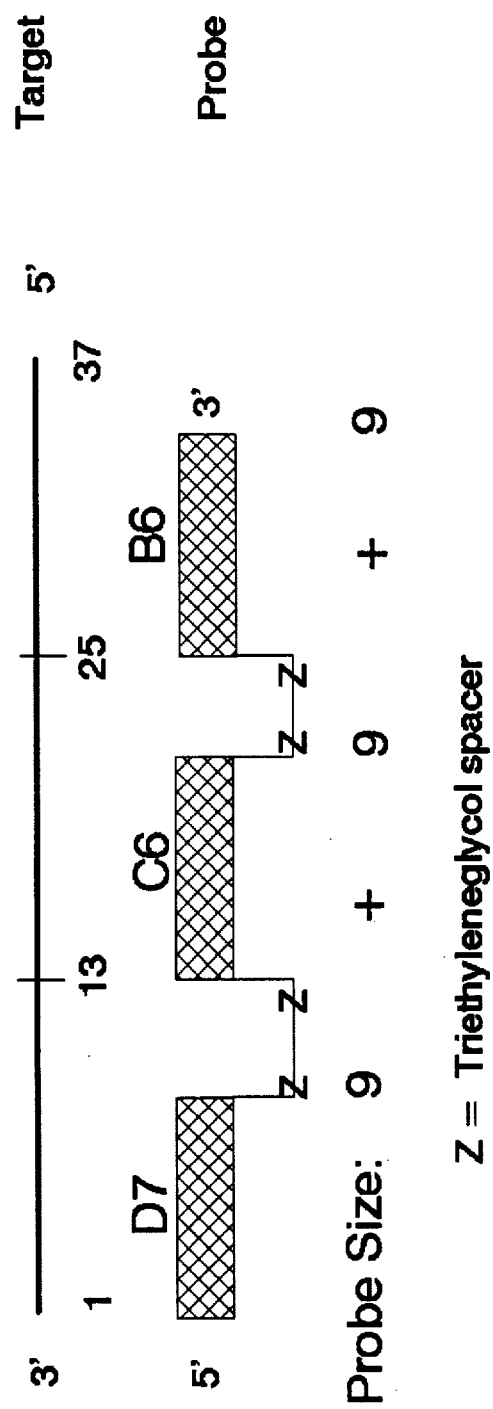
FIG. 6 shows the design of an experiment to study the effects of discontinuous probe design to optimize target binding.

Several of the secondary hybritopes analyzed in Example 3 were used as the basis for a discontinuous probe design as schematized in FIG. 6. A 37-mer region of the HIV RRE was studied using secondary hybritopes of varying lengths corresponding to B6, C6 and D7, either joined continuously or with a

Figure 8:
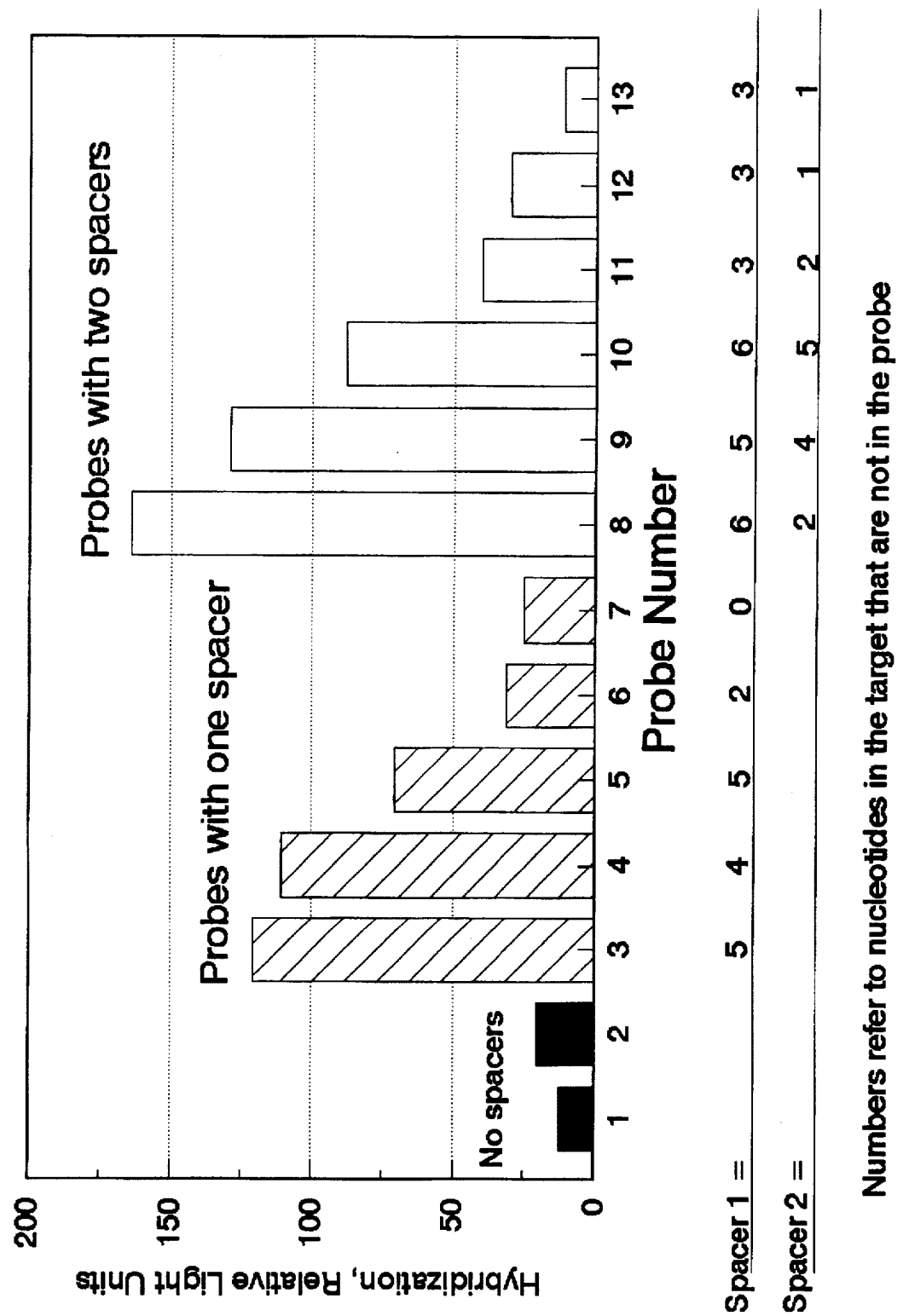

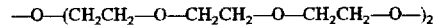

spacer ("Z—Z spacer") where there are intervening untargeted nucleotides as set forth in the chart in FIG. 7. For example, probe #1 in FIG. 7 is a continuous probe which hybridizes to nucleotides 1–25 of the target shown in FIG. 6. Probe #8 is a discontinuous probe containing three oligonucleotides corresponding to nucleotides 1–7, 14–23 and 26–34, each segment joined by a Z—Z spacer. The discontinuous probes also include the 5' GC rich region described in Example 1A. The results of the use of discontinuous probes in the assay of Example 2 are shown in FIG. 8. The results indicate that continuous probes with no spacers performed poorly, while probes discontinuous with 4–6 nucleotide spacing between hybridizing regions showed higher hybridization efficiencies than continuous probes with the same number of nucleotides.

The present invention has been described with reference to specific embodiments. However, this application is intended to cover those changes and substitutions which may be made by those skilled in the art without departing from the spirit and the scope of the appended claims.

---

We claim:

1. A method of determining a discontinuous probe that binds to a known nucleotide sequence in a target nucleic acid, the discontinuous probe comprising (i) at least two binding oligonucleotides that are each complementary to a distinct region of the target nucleic acid, which constitute the best target region for an oligonucleotide probe covalently joined optionally by (ii) an organic linker molecule the method comprising the steps of:

(a) determining at least first and second binding oligonucleotides that are complementary to first and second regions of the target nucleic acid, the first and second oligonucleotides binding more strongly to the target nucleic acid than other oligonucleotides that are complementary to other regions of the target nucleic acid and wherein the first and second regions are non-contiguous;

(b) covalently linking at least the first and second binding oligonucleotides determined in step (a) in at least two combinations optionally with organic linker molecules to obtain a set of candidate discontinuous probes;

(c) contacting each candidate discontinuous probe with the target nucleic acid under conditions permitting specific hybridization of oligonucleotides to the target: and (d) determining the presence or absence of specific discontinuous probe-target binding between each of the discontinuous probes and the target nucleic acid to indicate whether each discontinuous probe binds the target nucleic acid, thereby determining or detecting one or more discontinuous probes, wherein step (a) comprises the steps of ($a_1$) obtaining a plurality of oligonucleotides, each of the oligonucleotides comprising a first nucleotide sequence which is complementary to a sequence within the known nucleotide sequence, and the oligonucleotides having overlapping first nucleotide sequences wherein the first sequence of each of the oligonucleotides in the plurality of oligonucleotides overlaps the sequence of another oligonucleotide in the plurality of oligonucleotides by from one to four nucleotides;

($a_2$) contacting each of the oligonucleotides with the target nucleic acid under conditions permitting specific hybridization of oligonucleotides to the target;

($a_3$) determining the presence or absence of specific oligonucleotide-target binding between each of the oligonucleotides and the target nucleic acid to indicate whether each oligonucleotide binds within the known nucleotide sequence; and ($a_4$) selecting at least two binding oligonucleotides that bind most strongly to the target nucleic acid.

2. The method of claim 1 wherein the first sequence of each of the oligonucleotides in the plurality of oligonucleotides overlaps the first sequence of another oligonucleotide in the plurality of oligonucleotides by one nucleotide.

3. The method of claim 1 wherein each first sequence in the plurality of oligonucleotides is from 5 to 20 nucleotides in length.

4. The method of claim 3 wherein each first sequence in the plurality of oligonucleotides is from 8 to 12 nucleotides in length.

5. The method of claim 4 wherein each first sequence in the plurality of oligonucleotides is 10 nucleotides in length.

6. The method of claim 1, wherein step (a) further comprises, following step ($a_4$), the steps of:

(a$_5$) for each of the first and second binding oligonucleotides selected in step ($a_4$), obtaining a plurality of secondary oligonucleotides, each secondary oligonucleotide having a 5' end of its first sequence identical to the first sequence of selected oligonucleotide and having a sequence complementary to the same region of the target nucleic acid, wherein the length of the first sequence for each secondary nucleotide that is complementary to target nucleic acid is different than the first sequence length for the other nucleotides in the plurality of secondary nucleotides;

(a$_6$) contacting each of the secondary oligonucleotides with the target nucleic acid under conditions permitting specific hybridization of secondary oligonucleotides to the target;

(a$_7$) detecting or determining the presence or absence of specific secondary oligonucleotide-target binding between each of the secondary oligonucleotides and the target nucleic acid to indicate whether each secondary oligonucleotide binds within the known nucleotide sequence; and (a$_8$) for each of the first and second binding oligonucleotides, selecting the secondary oligonucleotide that binds most strongly to the target nucleic acid.

7. The method of claim 6 wherein the plurality of secondary nucleotides have a first sequence of between 6 and 20 nucleotides.

8. The method of claim 1 wherein the organic linker moieties are selected from the group consisting of arylene, $C_6$–$C_{18}$ aralkylene, $C_6$–$C_8$ aralkenylene, $C_6$–$C_{18}$ aralkynylene, $C_1$–$C_{30}$ alkylene, $C_1$–$C_{30}$ alkenylene, or $C_1$–$C_{30}$ alkynylene, containing 0 to 6 heteroatoms selected from the group consisting of O, S, N, Si and Se and 0 to 6 linkages selected from the group consisting of —CO—,
—COO—, —CONH—, —NHCO—, —S—S—, —SO$_2$—, —CH(OH)—CH(OH)—, —CH(OR$^1$)—CH(OR$^1$)—, —O—PO(O—)—O—, —O—PO(R$^1$)—, —O—PO(OR$^1$)—O—, —O—PO(OR$^1$)—R$^2$—, —PO(OR$^1$)—O—R$^2$ wherein R$^1$ is lower alkyl and R$^2$ is lower alkylene, —O—((CH$_2$)$_n$—A—)$_m$ and

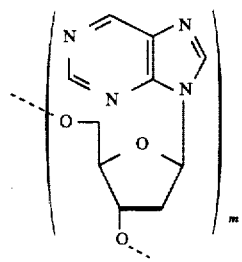

wherein —A— is —O— or —PO$_4$—, n is an integer from 2 to 4 and m is an integer from 1 to 20.

9. The method of claim 8 wherein the organic linker moieties have the formula —(CH$_2$CH$_2$—O—)$_m$—.

10. The method of claim 8 wherein the organic linker moieties have the formula —(CH$_2$CH$_2$—O—)$_{3m'}$—, where m' is an integer from 1 to 3.

11. The method of claim 8 wherein the organic linker moieties have the formula

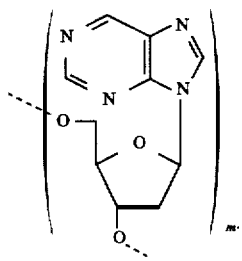

12. The method of claim 8 wherein the organic linker moieties are rigid and are selected from the group consisting of substituted or unsubstituted arylene, $C_6$–$C_{18}$ aralkylene, $C_6$–$C_{18}$ aralkenylene, $C_6$–$C_{18}$ aralkynylene, $C_1$–$C_{30}$ alkenylene, or $C_1$–$C_{30}$ alkynylene.

* * * * *